US009969512B2

(12) United States Patent
Eidebakken et al.

(10) Patent No.: US 9,969,512 B2
(45) Date of Patent: May 15, 2018

(54) DEVICE AND METHOD FOR STERLIZING PACKAGING CONTAINERS BY ELECTRON BEAM

(71) Applicant: Tetra Laval Holdings & Finance S.A., Pully (CH)

(72) Inventors: Roy Eidebakken, Veberod (SE); Jonas Dickner, Paarp (SE); Roger Lindgren, Sovde (SE); Hakan Mellbin, Horby (SE); Mats Akesson, Malmo (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 365 days.

(21) Appl. No.: 14/654,812

(22) PCT Filed: Dec. 17, 2013

(86) PCT No.: PCT/EP2013/076870
§ 371 (c)(1),
(2) Date: Jun. 22, 2015

(87) PCT Pub. No.: WO2014/095838
PCT Pub. Date: Jun. 26, 2014

(65) Prior Publication Data
US 2015/0336701 A1    Nov. 26, 2015

(30) Foreign Application Priority Data

Dec. 20, 2012 (EP) .................. 12198586
Jan. 17, 2013 (SE) .................. 1350054
(Continued)

(51) Int. Cl.
*B65B 55/08* (2006.01)
*A61L 2/08* (2006.01)

(52) U.S. Cl.
CPC ............. *B65B 55/08* (2013.01); *A61L 2/087* (2013.01); *A61L 2202/23* (2013.01)

(58) Field of Classification Search
CPC ... A61L 2/087; A61L 2202/23; B65B 55/025; B65B 55/027; B65B 55/08
See application file for complete search history.

(56) References Cited

U.S. PATENT DOCUMENTS

2006/0159583 A1    7/2006 Naslund et al.
2006/0284111 A1   12/2006 Naslund et al.
(Continued)

FOREIGN PATENT DOCUMENTS

EP       2 371 397 A1    10/2011
JP       2010058843 A     3/2010
(Continued)

OTHER PUBLICATIONS

International Search Report (PCT/ISA/210) dated Mar. 26, 2014, by the European Patent Office as the International Searching Authority for International Application No. PCT/EP2013/076870.

*Primary Examiner* — Timothy C Cleveland
(74) *Attorney, Agent, or Firm* — Buchanan Ingersoll & Rooney PC

(57) ABSTRACT

The invention relates to a sterilization device for sterilizing packaging containers with electron beams in a filling machine. The sterilization device comprises at least one first electron beam emitter adapted for sterilization of at least the interior of the packaging container and at least one electron beam emitter adapted for sterilization of at least the exterior of the packaging container. The invention further comprises a method for sterilizing packaging containers.

13 Claims, 11 Drawing Sheets

(30) Foreign Application Priority Data

| Feb. 1, 2013 | (SE) | 1350127 |
| Mar. 4, 2013 | (SE) | 1350256 |
| Jun. 25, 2013 | (SE) | 1350773 |

(56) References Cited

U.S. PATENT DOCUMENTS

| 2010/0054987 | A1 | 3/2010 | Krueger et al. |
| 2011/0012030 | A1 | 1/2011 | Bufano et al. |
| 2011/0012032 | A1 | 1/2011 | Bufano et al. |
| 2012/0219455 | A1 | 8/2012 | Meinzinger et al. |
| 2014/0117259 | A1 | 5/2014 | Holm et al. |

FOREIGN PATENT DOCUMENTS

| JP | 2011201600 A | 10/2011 |
| JP | 2012180129 A | 9/2012 |
| WO | WO 2004/110868 A1 | 12/2004 |
| WO | WO 2005/002973 A1 | 1/2005 |
| WO | WO 2010/102757 A2 | 3/2010 |
| WO | WO 2011/011079 A1 | 1/2011 |
| WO | WO 2013/004565 A1 | 1/2013 |

DEVICE AND METHOD FOR STERLIZING PACKAGING CONTAINERS BY ELECTRON BEAM

FIELD OF THE INVENTION

The present invention relates to a sterilization device for sterilizing packaging containers with electron beams. The invention also relates to a method.

BACKGROUND OF THE INVENTION

Within the food industry, it is common practice to pack liquid and partly liquid food products in packaging containers manufactured from a packaging laminate comprising a core layer of paper or paperboard and one or more barrier layers of, for example, polymer material or aluminium foil.

An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

When the top is finished the packaging container is ready to be filled with product through the still open bottom, and then sealed and finally folded. Before the filling operation the packaging container undergoes treatment. If distribution and storage is to be made in chilled temperature the packaging container is disinfected, whereas if distribution and storage is to be made in ambient temperature, the packaging container needs to be sterilized and the product needs to be processed so as to obtain sterility. Sterilization is a term referring to any process that eliminates or kills microbial life, including transmissible agents such as for example fungi, bacteria, viruses and spores, which may be present on a surface of the packaging material or in the product. Applied in the food packaging industry this is generally referred to as aseptic packaging, i.e. packaging sterilized products in sterilized packaging containers, i.e. keeping both the product and the packaging container free from living germs and microorganisms, so that the freshness of the product can be preserved without special cooling requirements, i.e. so that sterility can be maintained inside a packaging container although it is stored in ambient temperature. In the food packaging industry the term commercially sterile is also commonly used. According to Codex Alimentarius Commission ((WHO/FAO) CAC/RCP 40-1993) commercial sterility means "the absence of microorganisms capable of growing in the food at normal non-refrigerated conditions at which the food is likely to be held during manufacture, distribution and storage".

A conventional way of sterilizing a ready-to-fill packaging container is to use hydrogen peroxide, preferably in gas phase.

Another way to sterilize such packaging containers is to irradiate it by means of a low voltage electron beam emitted from an electron beam emitter. An example of linear irradiation by electron beam of ready-to-fill packaging containers is disclosed in the international patent publication WO 2005/002973. The electron beam emitter is cylindrical with an electron exit window positioned at one of the distal ends. The packaging container is lifted to surround the electron beam emitter during the sterilization cycle. Other examples of irradiation of packaging containers, in these cases PET bottles, are described in for example WO 2011/011079 and EP 2 371 397. In the disclosed systems emitters are used having a diameter small enough to be passed through a neck portion of the bottles.

SUMMARY OF THE INVENTION

The present invention relates to a sterilization device for sterilizing open packaging containers with electron beams. The sterilization device comprises a first chamber comprising at least one first electron beam emitter adapted for sterilization of at least the interior of the packaging container through an opening of the packaging container. It further comprises at least one second electron beam emitter adapted for sterilization of at least a portion of the exterior surface of said packaging container. The first chamber has an entry region towards a second chamber, through which entry region a packaging container portion, comprising said opening, is adapted to be passed for entrance into the second chamber. The at least one second electron beam emitter is arranged such that its electron exit window is at least substantially facing said entry region, said second electron beam emitter thereby being adapted to sterilize at least any exterior surface of the packaging container portion being passed through the entry region. The at least one first electron beam emitter is arranged to sterilize the interior surface before or at the same time as said packaging container portion is entered into the second chamber.

With a sterilization device of the present invention it is possible to sterilize the interior and exterior surfaces of the packaging containers with separate electron beam devices, yet being able to ensure sterility by having the interior and exterior sterilization made at least partly simultaneously. If the interior and exterior sterilization is separated in time it may be more difficult to ensure sterility. If separated in time microbiological material may have a chance to find its way from a not-yet-sterilized surface to an already sterilized surface.

Further, with a sterilization device of the present invention a clear aseptic barrier is achieved in the packaging container passage into the aseptic chamber. Hence, there is created a passage into the aseptic chamber for packaging containers, or portions thereof, but the passage is protected by an electron cloud such that anything being transported through that passage will be sterilized before being entered into that aseptic chamber.

In one or more embodiments the first electron beam emitter and the packaging container are adapted to perform a mutual relative movement, during which movement a portion of the first electron beam emitter is temporarily inserted through the opening of the packaging container, such that interior sterilization of the packaging container takes place.

Further, in one or more embodiment the at least one second electron beam emitter is positioned such that an electron cloud emitted from the at least one second electron beam emitter, during operation of the sterilization device, is adapted to form an irradiation barrier at least covering the entry region.

In one or more embodiments an electron cloud emitted from the first electron beam emitter is adapted to temporarily meet and partly overlap the electron cloud emitted from the at least one second electron beam emitter, said electron clouds together forming a combined electron cloud, and the opening of the packaging container portion is at least temporarily positioned within the combined cloud.

In one or more further embodiments the electron cloud of the at least one second electron beam emitter is elongate and defines the entry region, and the entry region is being inclined in relation to a feeding direction of the packaging containers and in relation to a longitudinal direction of the packaging containers, such that a greater exterior surface area of the packaging containers passing through the entry region are sterilized.

In one or more embodiments the at least one second electron beam emitter is arranged such that a longitudinal axis thereof and of the electron exit window is inclined in relation to a horizontal direction, and the packaging container is moved along said horizontal direction, with a longitudinal centre axis of the packaging container directed perpendicular to the horizontal direction, in such a way that a portion of the packaging container, comprising the opening, is gradually leaving the entry region and entering the second chamber.

In one or more additional embodiments the second chamber has a bottom wall provided with a slot, and the packaging containers are transported in the second chamber along the slot having the sterilized packaging container portion positioned above said bottom wall, and the rest of the packaging container positioned below said bottom wall, and wherein a sterile gas flow is provided, during operation, from the second chamber and in a direction towards the slot.

In one or more embodiments the second chamber is an aseptic chamber.

In one or more embodiments the second chamber comprises at least one filling station for filling content into the packaging container, and at least one station for sealing the opening after filling.

Further, in one or more embodiments it comprises two second electron beam emitters, arranged opposite each other with their electron exit windows facing each other and the entry region, in such a way that the packaging containers can pass in between them.

In one or more embodiments more than one first electron beam emitter is stationary arranged on a rotatable carrier wheel.

In one or more further embodiments the sterilization device comprises a packaging container conveying system comprising a packaging container conveyor comprising holders adapted to hold the packaging containers, and said packaging container conveyor is used for transporting packaging containers both in the first chamber, the entry region and the second chamber.

In one or more additional embodiments the packaging container conveying system comprises a rotatable guide wheel adapted to cooperate with the carrier wheel and the packaging container conveyor such that each packaging container is adapted to be aligned with a first electron beam emitter, and which guide wheel is provided with packaging container grippers adapted to displace the packaging container in relation to the first electron beam emitter between a first position in which the packaging container and the first electron beam emitter are not engaged with each other and a second position in which the first electron beam emitter is fully inserted into the packaging container.

In one or more embodiments the packaging container gripper is adapted to lift the packaging container from the holder to the second position, in which the packaging container is released from the holder, and then to retract the packaging container to the first position and back into the same holder.

In one or more embodiments the relative movement is such that the packaging container is moved with a first velocity from the first position to the second position, and with a second velocity from the second position back to the first position, said second velocity being lower than the first velocity.

In one or more embodiments the sterilization device is arranged in a filling machine.

In one or more embodiments the second chamber comprises at least one filling station for filling content into the packaging container, and at least one station for sealing the opening after filling.

The invention also comprises a method of sterilizing open packaging containers with electron beams. The method comprises sterilizing at least the interior of the packaging container, through an opening of the packaging container, with a first electron beam emitter arranged in a first chamber. It also comprises sterilizing at least a portion of the exterior of the packaging container with at least one second electron beam emitter, wherein said at least one second electron beam emitter being arranged such that its electron exit window is at least substantially facing an entry region, said entry region forming an entrance to a second chamber from the first chamber. The step of sterilizing at least a portion of the exterior of the packaging container is performed in said entry region by passing a portion of the packaging container, said portion comprising said opening, through the entry region. The step of sterilizing the interior of the packaging container is performed before or at the same time as said packaging container portion is entered into the second chamber.

In one or more embodiments the method comprises performing a mutual relative movement between the first electron beam emitter and the packaging container during which movement the step of sterilizing the interior of the packaging container takes place, and during which movement a portion of the first electron beam emitter is temporary inserted through the opening of the packaging container.

In one or more further embodiments the method comprises forming an irradiation barrier at least covering the entry region during operation of the sterilizing device, said irradiation barrier being formed by an electron cloud emitted from the at least one second electron beam emitter.

In one or more embodiments the method comprises forming a combined electron cloud by temporarily letting an electron cloud emitted from the first electron beam emitter meet and partly overlap the electron cloud emitted from the at least one second electron beam emitter, and temporarily positioning the opening of the packaging container within the combined electron cloud.

In one or more embodiments the steps are performed in a filling machine.

In one or more embodiments the method comprises the additional steps of filling content into the sterilized packaging container, and sealing the opening after filling.

BRIEF DESCRIPTION OF THE DRAWINGS

In the following, an embodiment of the invention will be described in greater detail, with reference to the enclosed schematic drawings, in which.

DETAILED DESCRIPTION OF A PREFERRED EMBODIMENT

Figure 1A:
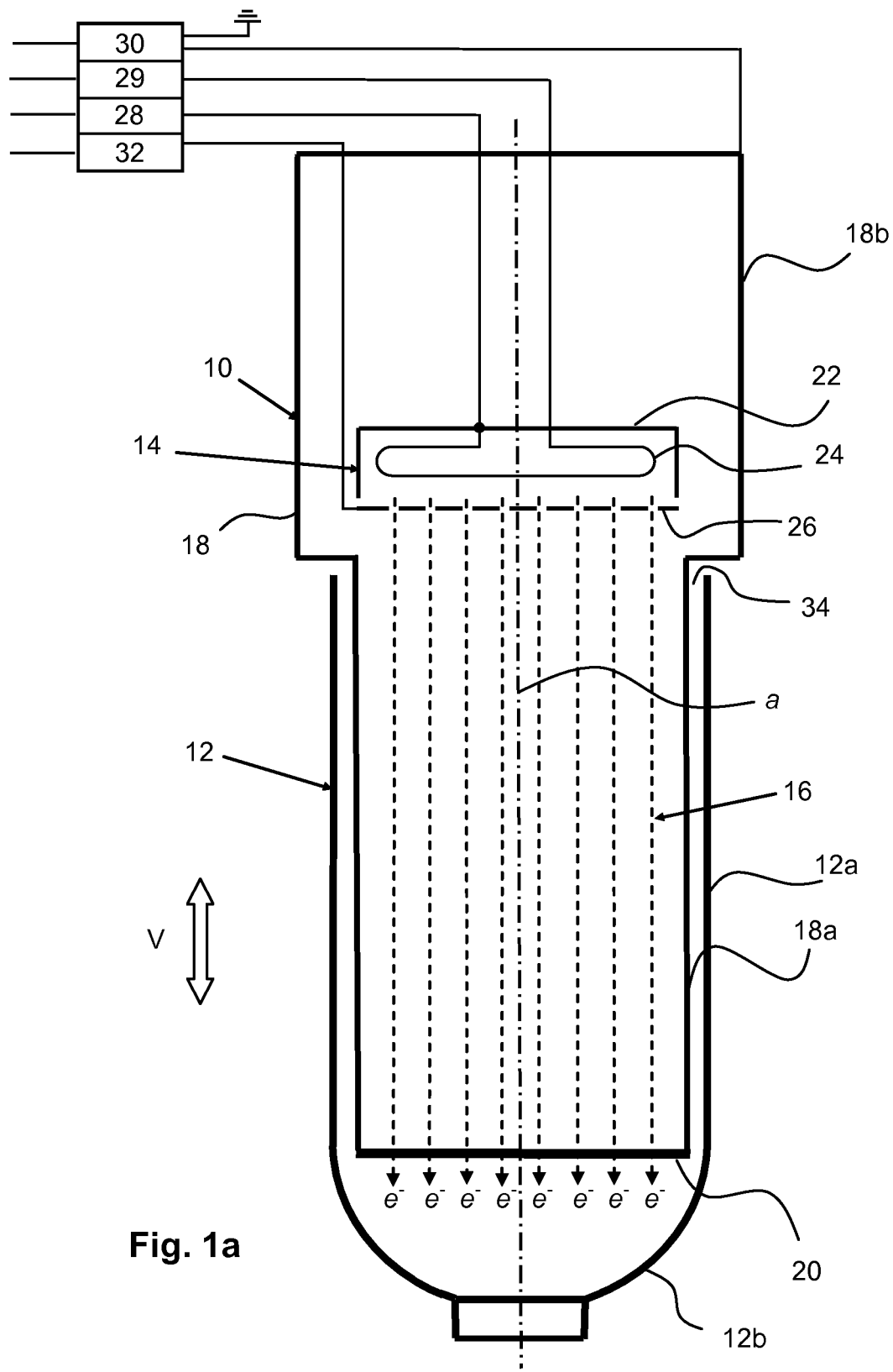
FIG. 1a is a side view of a packaging container and an exemplary first electron beam emitter, for sterilizing the interior of the packaging container, in a fully engaged sterilization position.

When irradiating packaging containers of bottle-type, as described in the introduction, two types of electron beam emitters can typically be employed. One is being used for interior sterilization and the other for exterior sterilization.

In the following, and with reference to FIG. 1a, an exemplary first electron beam emitter 10 for sterilizing the interior of ready-to-fill packaging containers 12 will be described. Such electron beam emitter has been previously described in for example the international publication WO2010/040453.

The electron beam emitter 10 comprises an electron generator 14 for emitting a substantially circular electron beam 16 along a path. The electron generator 14 is enclosed in a hermetically sealed vacuum chamber 18. Said vacuum chamber 18 is provided with an electron exit window 20.

The electron generator 14 comprises a cathode housing 22 and a filament 24. In use, an electron beam 16 is generated by heating the filament 24. When an electrical current is fed through the filament 24, the electrical resistance of the filament 24 causes the filament to be heated to a temperature in the order of 2000° C. This heating causes the filament 24 to emit a cloud of electrons. The electrons are accelerated towards the electron exit window 20 by means of a high-voltage potential between the cathode housing 22 and the exit window 20 (being the anode). Subsequently, the electrons pass through the electron exit window 20 and continue towards the target area, i.e. in this case the inside of the packaging container 12.

The filament 24 can be made of tungsten. The grid 26, placed between the filament 24 and an electron beam exit window 20, is provided with a number of openings and is used for diffusing the electron beam 16 into a more uniform beam, and for focusing the electron beam 16 towards the target area.

The high-voltage potential is created by for example connecting the cathode housing 22 and the filament 24 to a power supply 28 and by connecting the vacuum chamber to ground 30. The filament also needs a second connection 29. The first electron beam emitter 10 is generally denoted low voltage electron beam emitter if the voltage is below 300 kV. For sterilization of packaging containers operating voltages in the order of 50-150 kV is conventionally used. In the disclosed design the accelerating voltage is in the order of 90-100 kV. This voltage results in a kinetic (motive) energy of 95 keV in respect of each electron. However, another voltage can be chosen, for example in the interval 75-150 kV. By applying an electrical potential also to the previously mentioned control grid 26 the emission of electrons may be further controlled. If a separate and variable electrical potential is applied to the control grid 26 it makes it possible to use the control grid 26 for active shaping of the generated electron beam. For these purposes the control grid 26 may be electrically connected to a separate power supply 32.

The emitter 10 is, as mentioned, further provided with an electron exit window 20. The window 20 can be made of a metallic foil, such as for example titanium, and can have a thickness in the order of 4-12 µm. A supporting net (not shown) formed of aluminum or copper supports the foil from inside the vacuum chamber 18. The electrons are exiting the vacuum chamber 18 through the exit window 20.

In this embodiment the vacuum chamber 18 is made up of two elongate cylindrical bodies 18a, 18b with substantially circular cross sections. The cylindrical bodies have a common longitudinal centre axis a. The first cylindrical body 18a has an end surface, in a plane being perpendicular to the centre axis a, being provided with the electron exit window 20. The electron exit window is circular and preferably extends over most of the end surface. The diameter of said first body 18a is small enough to be inserted into the ready-to-fill packaging container 12, the cross section of said first body is dimensioned such that it can be guided through an opening 34 of the packaging container 12. The second body 18b is provided with the electron beam generator 14, and the diameter of said second body 18b is larger than the first body 18a. The diameter of the emitted electron beam 16, while still inside the emitter 10, is smaller than the diameter of the first body 18a.

Figure 1B:
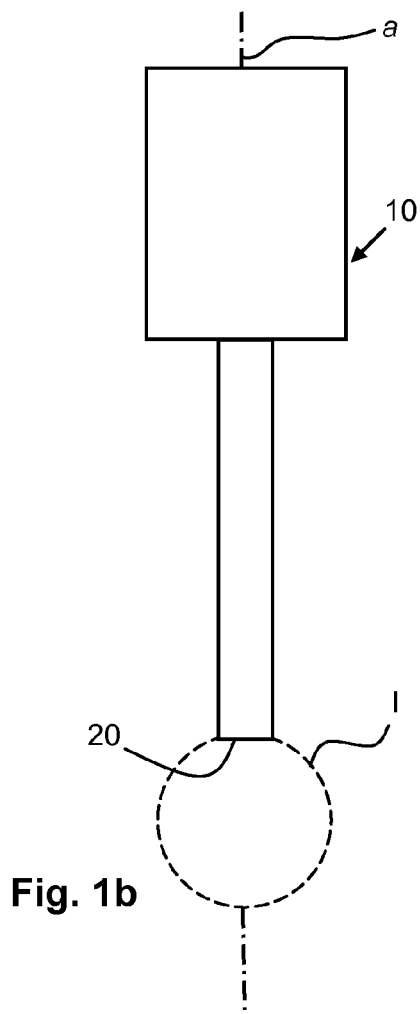
FIG. 1b is a side view of the first electron beam emitter and its electron cloud.

The first electron beam emitter 10 emits, from its electron exit window 20, a first electron cloud I illustrated schematically by a dashed line in FIG. 1b. The cross sectional shape is circular, as shown, or droplet-shaped. The shape of the electron cloud is defined by the shape of the window and by the Brownian motion of individual electrons leaving the electron exit window. The electron cloud is axis-symmetrical, around axis a, and the cloud volume is thereby spherical (or droplet-shaped). The dose rate at the boundary of the electron cloud I is approx. 1000-1600 kGy/s. In the centre of the electron cloud the dose rate is higher. The energy of the first electron beam emitter 10 needs to be matched with the sterilization time available, the packaging container size and shape, the packaging container velocity relative the electron beam emitter, and the above number should be seen purely as an example.

In FIG. 1a packaging container 12 is shown which is in a shape ready to be filled with product through the opening 34. It comprises a sleeve body 12a and a top portion 12b. The top portion comprises a neck or spout sealed with a screw cap. The sleeve body 12a is provided with the opening 34.

Figure 1C:
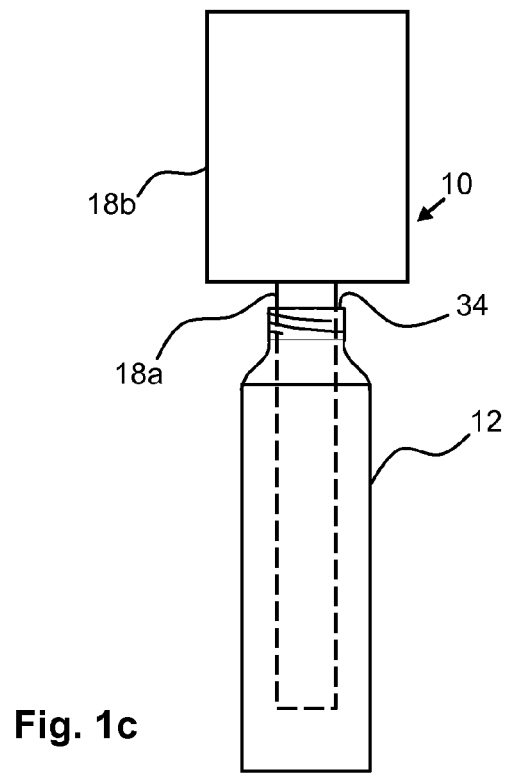
FIG. 1c is a view of an alternative packaging container and first electron beam emitter.

In FIG. 1a the opening 34 of the packaging container 12 is an open bottom end, which after filling will be sealed and folded to form a substantially flat bottom surface. It should however be understood that this opening 34, through which the first electron beam device 10 is received and through which filling will be made, may in other embodiments be arranged in the top of the packaging container, provided by a neck or spout portion of the packaging container 12. FIG. 1c illustrates such embodiment. The neck or spout portion will, after filling, be sealed by for instance a screw cap.

A typical electron beam emitter for interior sterilization has now been described. In the following a typical electron beam emitter for exterior sterilization of ready-to-fill packaging containers will be described. Such electron beam emitter may also be used for web sterilization, as described for example in the international publication WO2004/110868, and has previously been described in for example the international publication WO2013/004565.

Figure 2A:
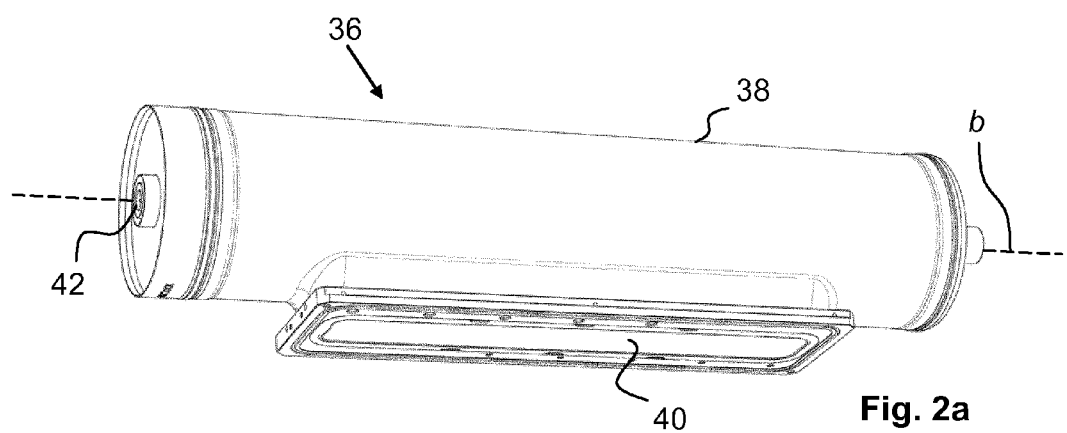
FIG. 2a is a perspective view of a second electron beam emitter for sterilizing the exterior of the packaging container.

In FIG. 2a an exemplary hermetically sealed second electron beam emitter 36 for exterior sterilization is shown. The purpose of the drawing is simply to illustrate the basic components of the emitter, and it should be emphasized that the purpose is not to provide a true constructional drawing or in any other way limit the present invention.

The main component of the electron beam emitter is the tubular body 38, which has an elongate shape along the longitudinal centre axis b. An electron exit window 40 provides an outlet for electrons from the vacuum inside the tubular body 38. The electron exit window 40 is substantially rectangular having its longest extension in a direction along the longitudinal centre axis b. The electron exit window 40 is substantially flat and protrude from the perimeter surface of the tubular body 38. The window 40 can be made of a metallic foil, such as for example titanium, and can have a thickness in the order of 4-12 µm. A supporting structure (not shown) provided with holes supports the foil from inside the vacuum chamber. The supporting structure is for example made of aluminium or copper.

The exit window 40 comprises subassemblies not relevant for the present invention, yet having the properties of providing an outlet window for electrons while maintaining vacuum inside the body 38. An exemplary electron exit window that can be used is described in the international publication No. WO2010/102757.

A proximal end of the body 38 comprises an assembly including electrical connections 42.

Figure 2B:
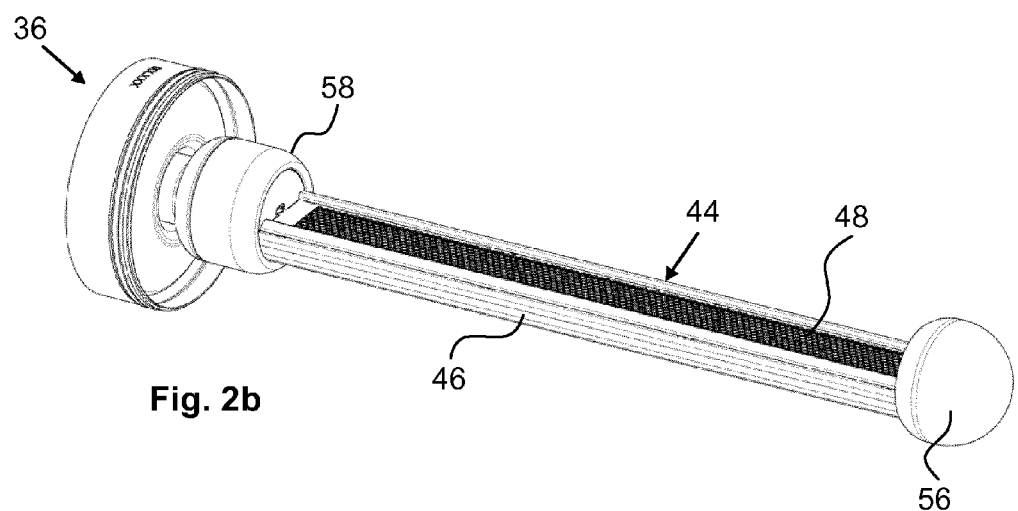
FIG. 2b is a perspective view of a cathode which may be used in the electron beam emitter of FIG. 2a, FIG. 2c is a cross section of the cathode of FIG. 2b.
Figure 2C:
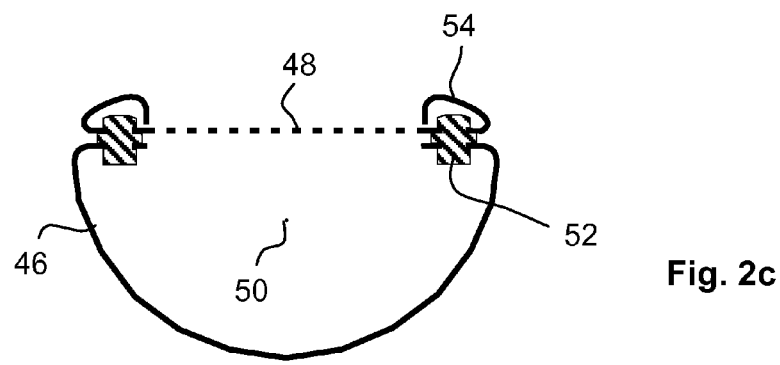
FIG. 2d is a side view of the second electron beam emitter and its electron cloud.
FIG. 2e is a schematic front view of the second electron beam emitter and its electron cloud.
FIG. 2f is side view showing two oppositely arranged second electron beam emitters.
FIG. 2g is a side view of two second electron beam emitters having electron exit windows being inclined relative each other.

FIG. 2b shows the emitter 36 without the tubular body 38, and a cathode 44 is shown. The cathode 44 comprises a cathode housing 46, which is also shown in the very schematic cross section of FIG. 2c. The cathode housing 46 is formed as a semi-annular shell, the open side of which is covered by a control grid 48. Inside the annular shell of the cathode housing 46 one or more filaments 50 (see FIG. 2c) are arranged, extending from a proximal end of the cathode housing 46 to a distal end thereof. In use, an electron beam is generated by heating the filament 50, using a current, and by accelerating the electron towards the electron exit window 40 by means of a high-voltage potential between the cathode housing 46 and the exit window 40 (being the anode), i.e. the same process as for the electron beam device of FIG. 1a. The high-voltage potential is created by for example connecting the cathode housing to a power supply and by connecting the tubular body 38 to ground. By applying an electrical potential also to the control grid 48 the emission of electrons may be further controlled. This can be achieved by connecting the control grid 48 to a separate power supply.

The control grid 48 comprises a flat perforated surface comprising a pattern of openings or through-holes for passage of electrons. The open side of the cathode housing 46, carrying the control grid 48, should for obvious reasons be facing the electron exit window 40. The cathode housing 46 and the control grid 48 are mounted together by means of attachment means 52. If there is a difference in electrical potential between the cathode housing 46 and the grid 48 said attachment means 52 are preferably electrical isolator elements. Free longitudinal end portions 54 of the control grid 48 are bent in a direction towards each other, i.e. in a lateral direction being perpendicular to the extension of the longitudinal end portions, to form bulge-like shapes for the formation of electron beam shaping electrodes. Such electrodes are sometimes referred to as "Wehnelt" electrodes. The bulge-like shape will assist in the generation of a smooth predictable electrical field to the benefit of performance of the electron beam emitter. They help shaping the electric field so that the electrons will hit the exit window 40 in an essentially right angle, i.e. in a direction essentially perpendicular to the plane of the exit window 40.

The described cathode is fitted into the electron beam emitter as shown in FIG. 2b. The proximal end as well as the distal end of the cathode housing 46 comprises electrical connections as well as physical suspensions for the filament 50. At the distal end this arrangement is housed inside or covered with a dome-shaped cap 56. At its proximal end the cathode housing 46 is suspended to the elongate body and the suspension is encapsulated by an annular cover 58.

This second electron beam emitter 36 has an accelerating voltage in the order of 95 kV. This voltage results in a kinetic (motive) energy of 95 keV in respect of each electron. However, another voltage can be chosen, for example in the interval 75-150 kV.

Figure 2D:
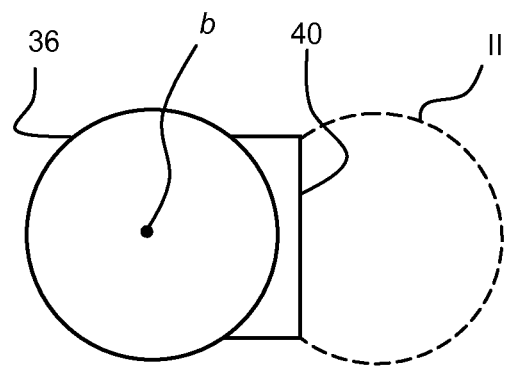
Figure 2E:
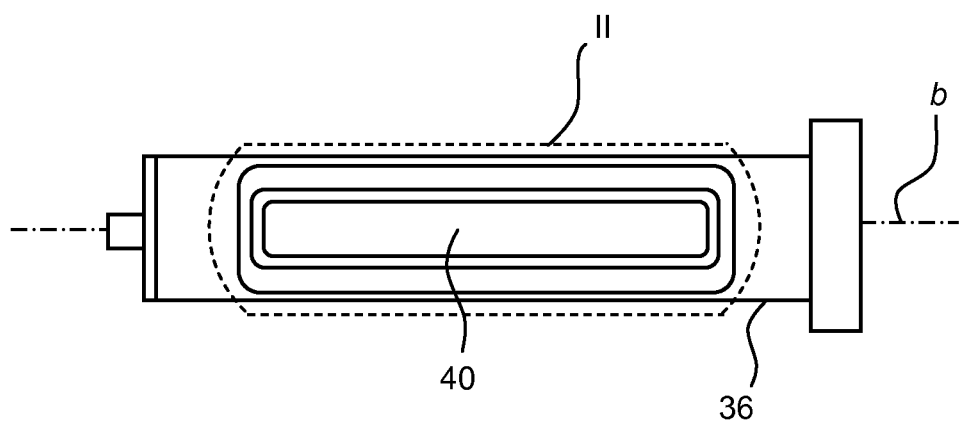

The electron cloud of the second electron beam emitter 36 is shown in FIGS. 2d and 2e, denoted II and represented by a dashed line. The cloud II has a substantially circular cross section in a plane perpendicular to the longitudinal axis b, see FIG. 2d. Further, seen in FIG. 2e, the cloud II has a somewhat rectangular or rounded cross section in a plane parallel to the electron exit window. Thus the electron cloud II has an extension in three dimensions and forms a volume in front of, and covering, the electron exit window 40. The dose rate at the boundary of the electron cloud II is approx. 400-800 kGy/s. In the centre of the electron cloud II the dose rate is higher.

Figure 2F:
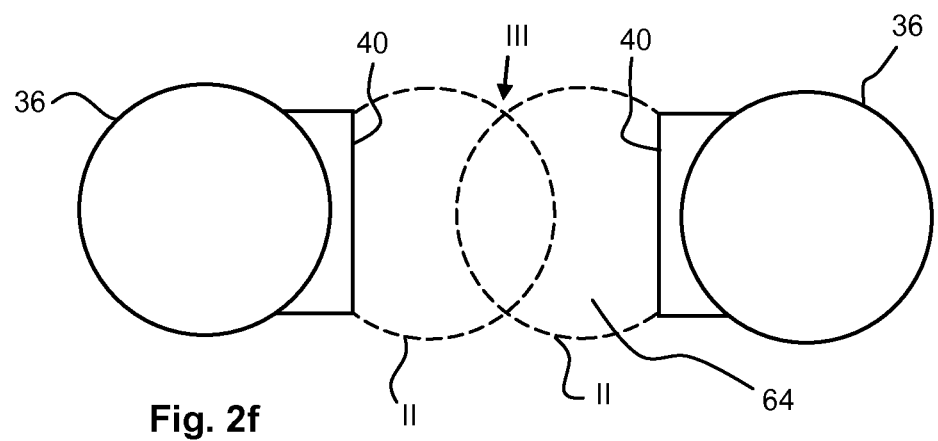
Figure 2G:
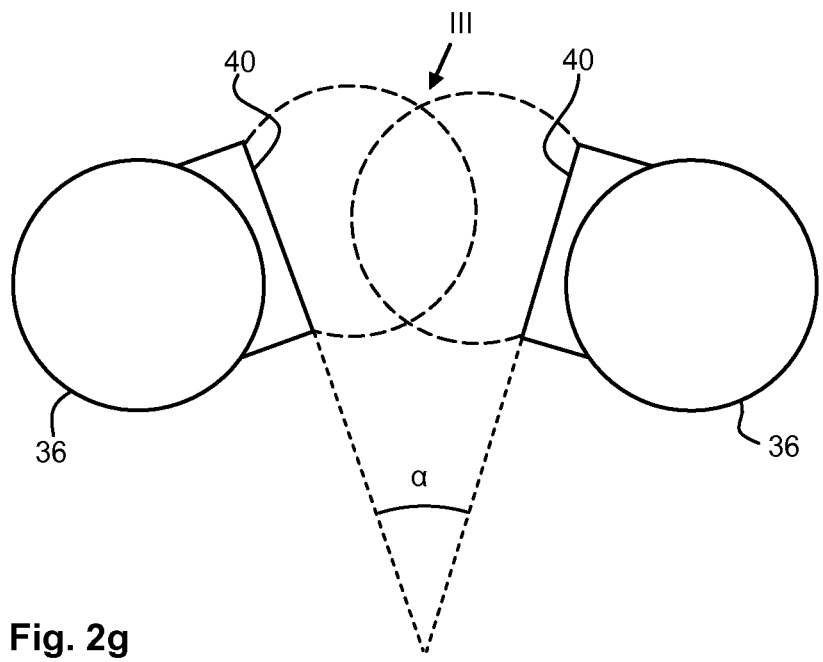

Two second electron beam emitters 36 can be arranged opposite each other, with their electron exit windows 40 facing each other, forming a gap in between them. Such an arrangement is shown in FIG. 2f. The electron beams generated by the second electron beam emitters 36 overlap each other and form a total electron cloud III. The boundary of the cross section of that electron cloud is shown with dashed line. The total electron cloud III fills the gap. Either the planes of the electron exit windows 40 are parallel to each other, as seen in FIG. 2f, or are slightly inclined in relation to each other as shown in FIG. 2g. In the latter case the inclination may be defined by an angle α between the two electron exit windows 40.

Figure 3A:
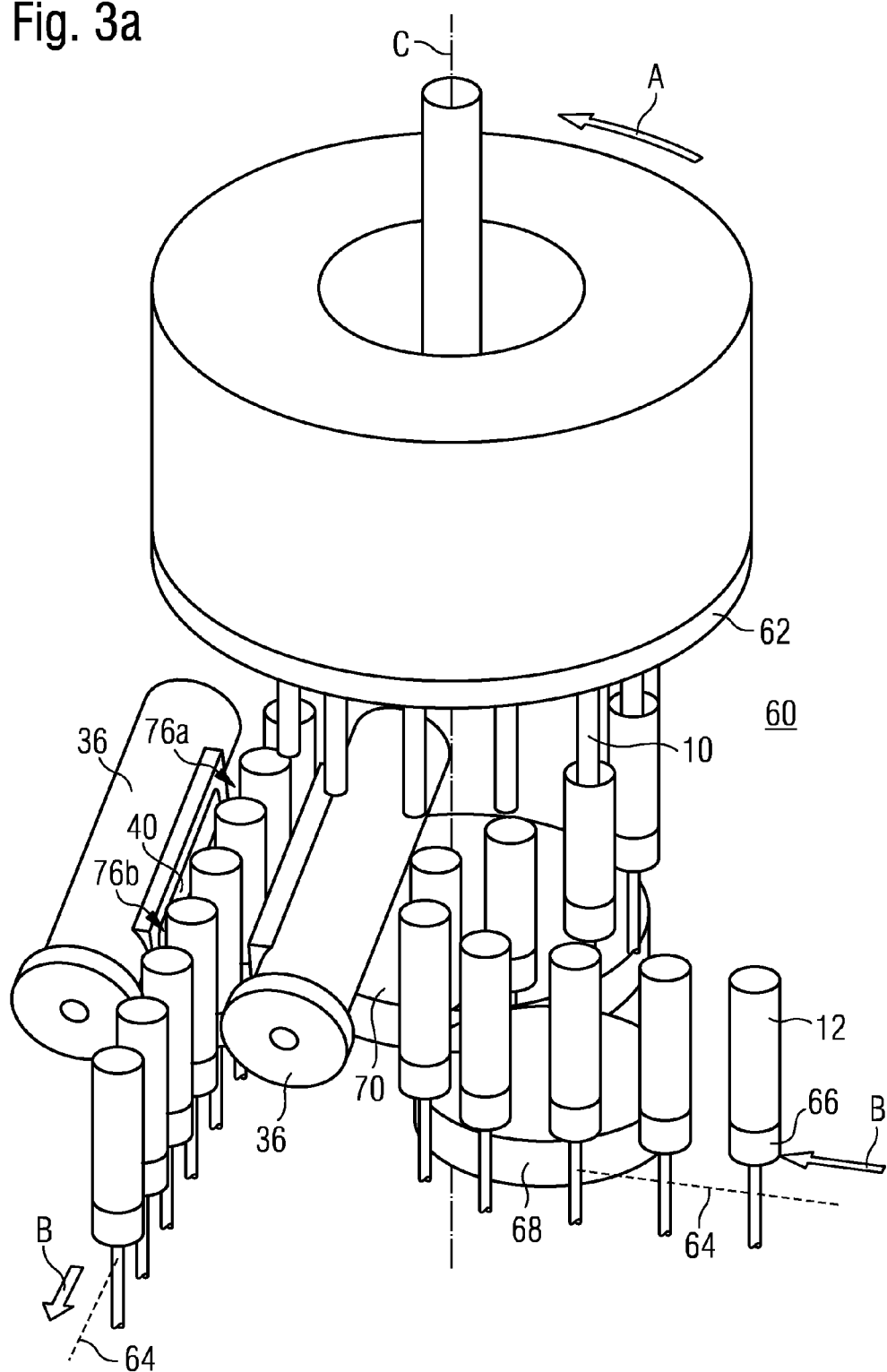
FIG. 3a is a perspective view of the sterilization device according to an exemplary embodiment of the invention.

FIG. 3a shows a perspective view of an embodiment of the sterilization device of the present invention. The object of the sterilization device is to sterilize ready-to-fill packaging containers in a filling machine. It is positioned downstream of the module manufacturing the open packaging container. In carton bottle machines this module comprises sub-modules in which packaging laminate blanks are formed into sleeves and provided with top portions being injection moulded. In case of a PET-bottle machine this module may include a blow-moulding device. Upstream in the filling machine, i.e. after the sterilization device, a filling module is provided for filling a product into the packaging container and a sealing module for sealing the packaging container after filling.

In this embodiment the sterilization device comprises a first chamber, denoted 60, being a sterilization chamber in which interior sterilization of the packaging containers 12 is to be performed. The first chamber 60 will hereinafter be referred to as sterilization chamber. The sterilization chamber 60 is provided with several first electron beam emitters 10, of the type described above with reference to for example FIG. 1a, arranged on a rotatable carrier wheel 62. Only the lower portions 18a of the first electron beam emitters 10 are shown in the figure. In this example twelve first electron beam emitters 10 are provided, but the number may be changed depending on the application (capacity, package size etc). The first electron beam emitters 10 are arranged evenly distributed near the perimeter of the carrier wheel 62 with their longitudinal centre axes a parallel to a centre rotation axis c of the carrier wheel 62. The direction of the rotation is represented by arrow A. The first emitters 10 are arranged with their electron exit windows 20 directed downwards in the figure and aligned with a virtual horizontal plane. Further, the first electron beam emitters 10 are stationary arranged on the carrier wheel 62 such that they will follow the rotation of the carrier wheel 62.

Further, the sterilization device is provided with a first conveyor 64 for conveying packaging containers 12 through the sterilization device. The first conveyor may be comprised by two or more co-operating conveyors or may, as in this embodiment, comprise one single conveyor.

In this exemplary embodiment the conveyor, represented by the dashed line 64, is a belt or chain provided with packaging container holders 66. The holders 66 are only very schematically shown. The packaging container 12 is adapted to be arranged in the packaging container holder 66 such that its open bottom end is directed upwards, in a direction facing the electron exit window 20 of the first electron beam emitter 10, as seen in for example FIG. 1a. The holder 66 will grip the packaging container around its sleeve 12a, near the top portion 12b of the packaging container 12. This conveyor 64 can of course be designed in any conventional way.

The movement of the belt or chain is continuous in the present embodiment, may be intermittent in other embodiments. The direction of the movement is illustrated by the arrow B.

At a packaging container in-feed, where the packaging container enters the sterilization chamber 60, the first conveyor 64 is guided along the perimeter of a packaging container in-feed wheel 68. Said in-feed wheel 68 cooperates with a guiding wheel 70. The guide wheel 70 is arranged underneath the carrier wheel 62 and has its centre rotation axis aligned with the centre rotation axis c of the carrier wheel 62.

Figure 3B:
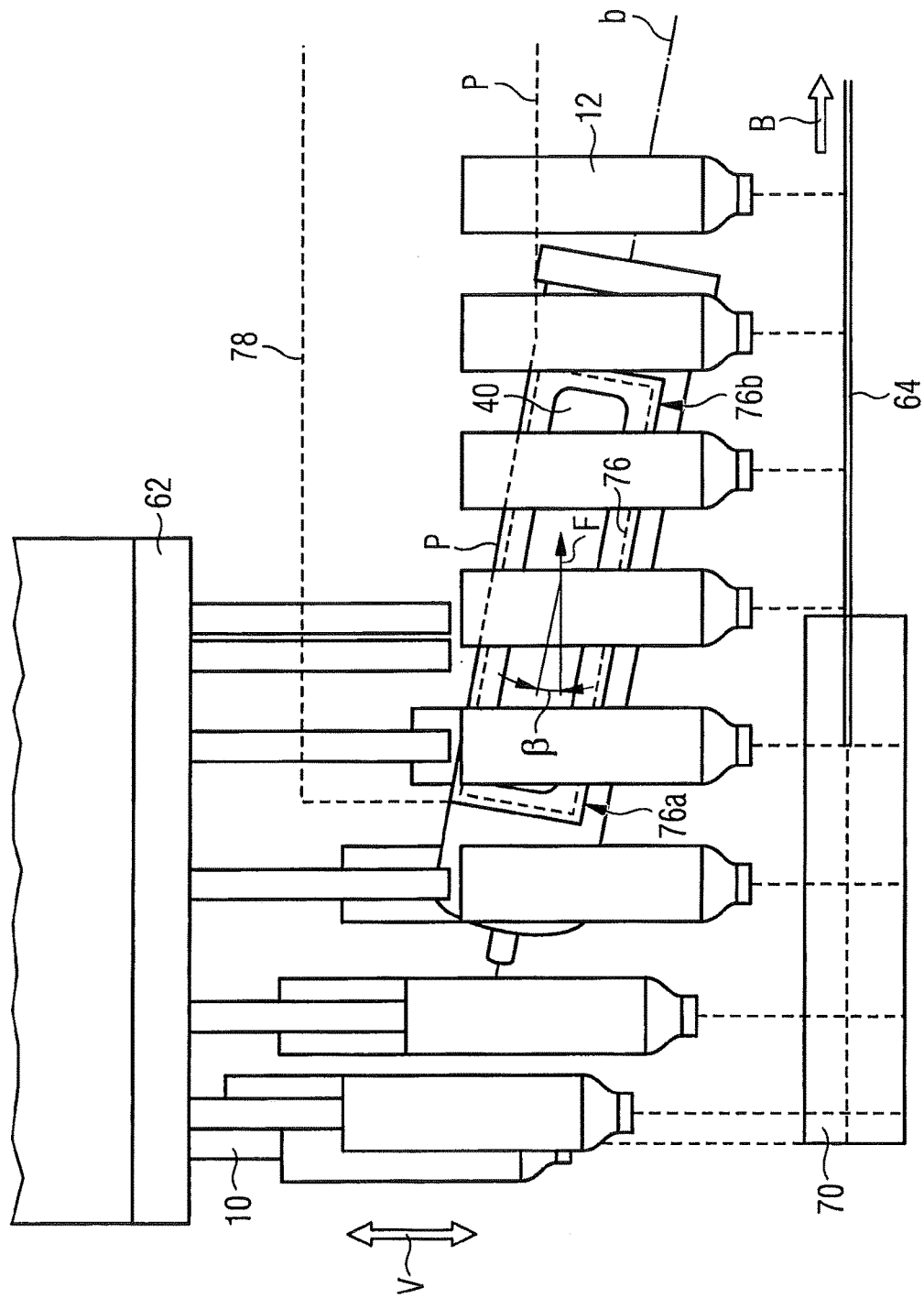
FIG. 3b is a side view of parts of the sterilization device illustrating the movement of the packaging containers relative the electron beam emitters.
Figure 3C:
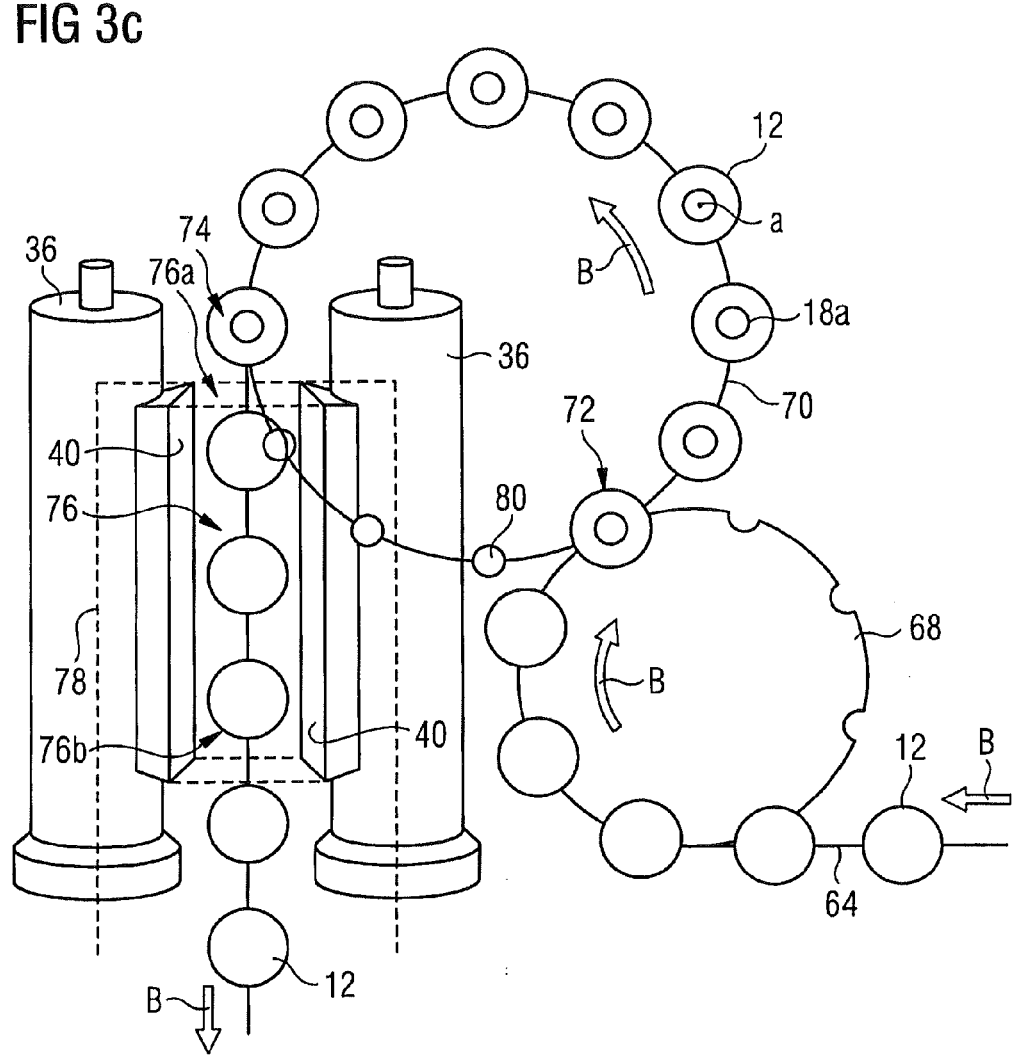
FIG. 3c is a top view showing parts of the sterilization device.

As mentioned, the first conveyor 64 is first guided by the in-feed wheel 68. Then it is tangentially transferred, as seen in FIG. 3c, at a packaging container sterilization in-feed position 72, over to the guide wheel 70. From the packaging container sterilization in-feed position 72 the first conveyor 64 is guided along the perimeter of the guide wheel 70. The guide wheel 70 is rotating, in relation to the carrier wheel 62, such that each packaging container 12 is synchronously moved with a first electron beam emitter 10, keeping the longitudinal axis a of the first electron beam emitter 10 aligned with a longitudinal axis of the packaging container 12, see common longitudinal axis a in FIG. 1a.

It should be noted that only the lower portions 18a of the first electron beam emitters 10 are visible in FIG. 3c.

The guiding wheel further has a packaging container out-feed position 74 at which the first conveyor 64 is tangentially directed away from the guide wheel 70 and towards an entry region 76 of a second chamber 78. The entry region 76 and the second chamber 78, represented in combination by the box sketched with dashed lines in FIG. 3a, will be described later.

The guide wheel 70 is provided with packaging container gripping means (not shown) which gripping means is adapted to cooperate with the first conveyor 64 around its perimeter. The guide wheel 70, with the packaging container grippers, and the first conveyor 64, with packaging container holders 66, are simultaneously moved, and each gripping means will be aligned with a respective holder 66 such that a packaging container 12 can be displaced from the holder 66 by the gripper and then back to the same holder.

The gripping means is adapted to vertically displace the packaging container 12 in relation to the first electron beam emitter 10. It displaces the packaging container 12 between a first position in which the packaging container 12 and the electron beam emitter 10 are not engaged with each other and a second position in which the packaging container 12 and the electron beam emitter 10 are fully engaged with each other. When the packaging container 12 and the electron beam emitter 10 are engaged the packaging container 12 has been raised to a position in which it partly encloses the electron beam emitter 10, i.e. the first electron beam emitter has been temporary inserted into the opening 34 of the packaging container 12. When they are not engaged the packaging container 12 is positioned underneath the electron beam emitter 10, i.e. the packaging container 12 has not started to surround the emitter 10, or has just been displaced down from the engaged position. At the in-feed position 72 and out-feed position 74 the packaging container 12 is positioned in the first position, i.e. not in engagement with the electron beam emitter 10. The relative movement between the first electron beam emitter 10 and the packaging container 12 is illustrated in FIG. 3b and the arrow V represents the vertical movement direction.

In this embodiment the electron beam emitters 10 are arranged stationary in the carrier wheel 62 and cannot move towards the packaging container 12. Due to their considerable weight, the fragile electron exit windows 20 and the high voltage connections it is an advantage to have the first electron beam emitters 10 stationary, and move the packaging containers 12 instead. However, in an alternative embodiment the electron beam emitter 10 is moved and the packaging container is stationary in the vertical direction. The electron beam emitter is hence lowered into the open end of the packaging container.

Preferably, each first electron beam emitter 10 is arranged with its first body 18a below the carrier wheel 62 and its second body 18b above the carrier wheel 62 together with any power transformers and high voltage connections (together represented as a cylinder in for example FIG. 3a).

The first electron beam emitter 10 is adapted to sterilize the interior surface of the packaging container 12 at least during a portion of the displacement from the in-feed position 72 to the out-feed position 74. The interior of the packaging container 12 corresponds to all inside surfaces of the packaging container 12. The interior sterilization is performed by means of the mutual relative movement between the first electron beam emitter 10 and the packaging container 12. As mentioned a portion of the first electron beam emitter is temporary inserted through the opening 34 of the packaging container 12 during the relative movement. At the in-feed position 72 the packaging containers 12, held by the packaging container holders 66 of the first conveyor, is aligned with a corresponding electron beam emitter 10 and is gripped by the gripping means. The gripping means preferably grips the packaging container 12 around the sleeve 12a. When the carrier wheel 62 rotates, so that the electron beam emitter 10 and packaging container 12 rotates from the in-feed position 72 to the out-feed position 74, the gripping means is adapted to raise the packaging container 12 towards the first electron beam emitter 10 for performing interior sterilisation. During that movement the packaging container 12 is temporary released from the holder 66 of the first conveyor 64. Since the first electron beam emitter 10 is aligned with the opening 34 of the packaging container 12 the electron beam emitter 10 is inserted in the packaging container 12. Hence, sterilization of the interior of the packaging container is commenced. Somewhere between the in-feed position 72 and the out-feed position 74 the packaging container has been displaced such that the packaging container 12 is fully engaged with the first electron beam emitter 10. In the fully engaged second position the first electron beam emitter 10 is fully inserted in the packaging container 12 as shown in FIG. 1a. This is also partly visible in FIG. 3b. In that position the innermost area of the packaging container 12 may be sterilized, in this case the top portion 12b of the packaging container 12.

The interior sterilization cycle is completed when the packaging container 12 reaches the out-feed position 74. When the packaging container 12 reaches said out-feed position 74, the packaging container 12 is retracted, or has already been retracted, from the second position back to the first position. The packaging container 12 is then ready to be fed out from the sterilization chamber 60.

The first electron beam emitters 10 are continuously operated, i.e. the electron emission is not shut off between sterilization cycles, i.e. it is kept in operation also in between two packaging containers being sterilized by the same electron beam emitter. Between the out-feed position 74 and the in-feed position 72 there is provided a position, denoted 80 in FIG. 3c, in which a sensor may be placed in front of the electron exit window 20 of any passing first electron beam emitters 10 in order to measure any dose control parameters.

The out-feed position 74 is arranged near the packaging container entry region 76 briefly mentioned above. At this entry region 76 the packaging containers 12 are adapted to partly enter the second chamber 78 being located downstream of the sterilization chamber 60. The entry region 76 is shown as a box indicated by dashed lines in FIGS. 3b and 3c. Hence, the packaging containers 12 will first be fed through the sterilization chamber 60 and then via the entry region 76 subsequently enter the second chamber 78 (also represented as a dashed box in the figures). In this embodiment the second chamber 78 is an aseptic chamber, and hereinafter it will be referred to as aseptic chamber 78. An aseptic chamber 78 is a chamber suitable for aseptic packaging as described in the introductory portion. During production of packaging containers 12 the environment in the aseptic chamber should be sterile, i.e. free from dirt and microbiological material. The aseptic chamber comprises stations (not shown) in which the packaging container 12 is adapted to be filled with a product, such as for example a beverage, and sealed. Depending on which end of the packaging container 12 that is open, the bottom as shown in FIG. 1a, or the neck as shown in FIG. 1b, the sealing station may look different. In the case of filling into an open bottom end the sealing station comprises sealing bars for heat sealing the packaging material. In the case of filling through a spout in a neck region of a packaging container the sealing station instead comprises a capping station.

Before the packaging containers 12 have been sealed it needs to be ensured that the environment around them is sterile, that the packaging containers 12 entering the aseptic chamber 78 from the sterilization chamber 60 are sterile, and that no contaminated air is allowed to escape into the aseptic chamber 78 from the sterilization chamber 60.

As mentioned above the guide wheel 70 further has a packaging container out-feed position 74, see for example FIG. 3c, at which the first conveyor 64 is tangentially directed away from the guide wheel 70 and towards the entry region 76. The entry region 76 forms an opening between the sterilization chamber 60 and the aseptic chamber 78. Said entry region correspond to a volume through which the packaging containers are transported before they enter the aseptic chamber 78. On each side of the opening two second electron beam emitters 36 are arranged. They are of the type described in relation to FIGS. 2a-2g, but may be of another suitable type. The two second electron beam emitters 36 are arranged opposite each other with their electron exit windows 40 facing each other and the volume of the entry region 76. Their longitudinal axes b are parallel to each other, but their electron exit windows 40 are slightly inclined in relation to each other as shown in FIG. 2g. The entry region 76, being the packaging container entrance, to the aseptic chamber 78 from the sterilization chamber 60, will during operation be totally covered by the unified electron cloud III of the two second emitters 36. Hence, the total cloud III forms an irradiation barrier or sterilization sluice at least covering the entry region 76, i.e. the unified cloud III forms an irradiated volume blocking the entrance to the aseptic chamber 78. The entry region 76 extends along the entire electron exit window 40, in a direction along the axis b, between a first end 76a and a second end 76b. The distance between the electron exit windows 40 is adapted to the size of the radial cross section of the packaging container 12, and should be kept only slightly larger such that the packaging container 12 can easily be passed between them.

As shown in FIG. 3a the second electron beam emitters 36 are positioned in a space between the first electron beam emitters 10 of the carrier wheel 62 and the guide wheel 70 carrying the gripping means. A portion of one of the second electron beam emitters 36 is located close to the centre of the guide wheel 70. This is to create a compact unit and to facilitate co-operation between the first and second electron beam emitters such that simultaneous sterilization can be obtained, as will be described later.

The entry region 76 formed between the electron exit windows 40 of the second electron beam emitters 36 is, as mentioned before, aligned with the first conveyor 64 extending tangentially from the packaging container out-feed point 74 on the guide wheel 70, and also tangentially from a virtual circle formed by the first electron beam emitters 10 as they rotate with the carrier wheel 62. The first electron beam emitters 36, rotating with the carrier wheel 62, are adapted to be moved near the first end 76a of the entry region 76 such that its electron cloud I at least partly moves into the entry region 76. Upon further rotation of the carrier wheel 62 the first electron beam emitter 10 is moved above the body 38 of the innermost second electron beam emitter 36. This is also shown in FIG. 3c, showing the entry region 76 and the electron beam emitters 36 from above.

As shown in FIG. 3b, the entry region 76 and the second electron beam emitters 36 (of which only one is shown in the figure) are inclined in relation to a feeding direction of the packaging containers. In this embodiment the feeding direction is horizontal and shown as an arrow F in the figure. The inclination is achieved in that the second electron beam emitters 36 are arranged such that the longitudinal axis b thereof, and of the electron exit window 40, is inclined an angle β in relation to the horizontal direction, and that the packaging containers are adapted to be moved along said horizontal direction F. Further, the packaging containers are moved along the horizontal direction with their longitudinal centre axes a directed perpendicular to said horizontal direction.

The sterilization device will now be further described in relation to the exterior sterilization of the packaging container 12.

Figure 3D:
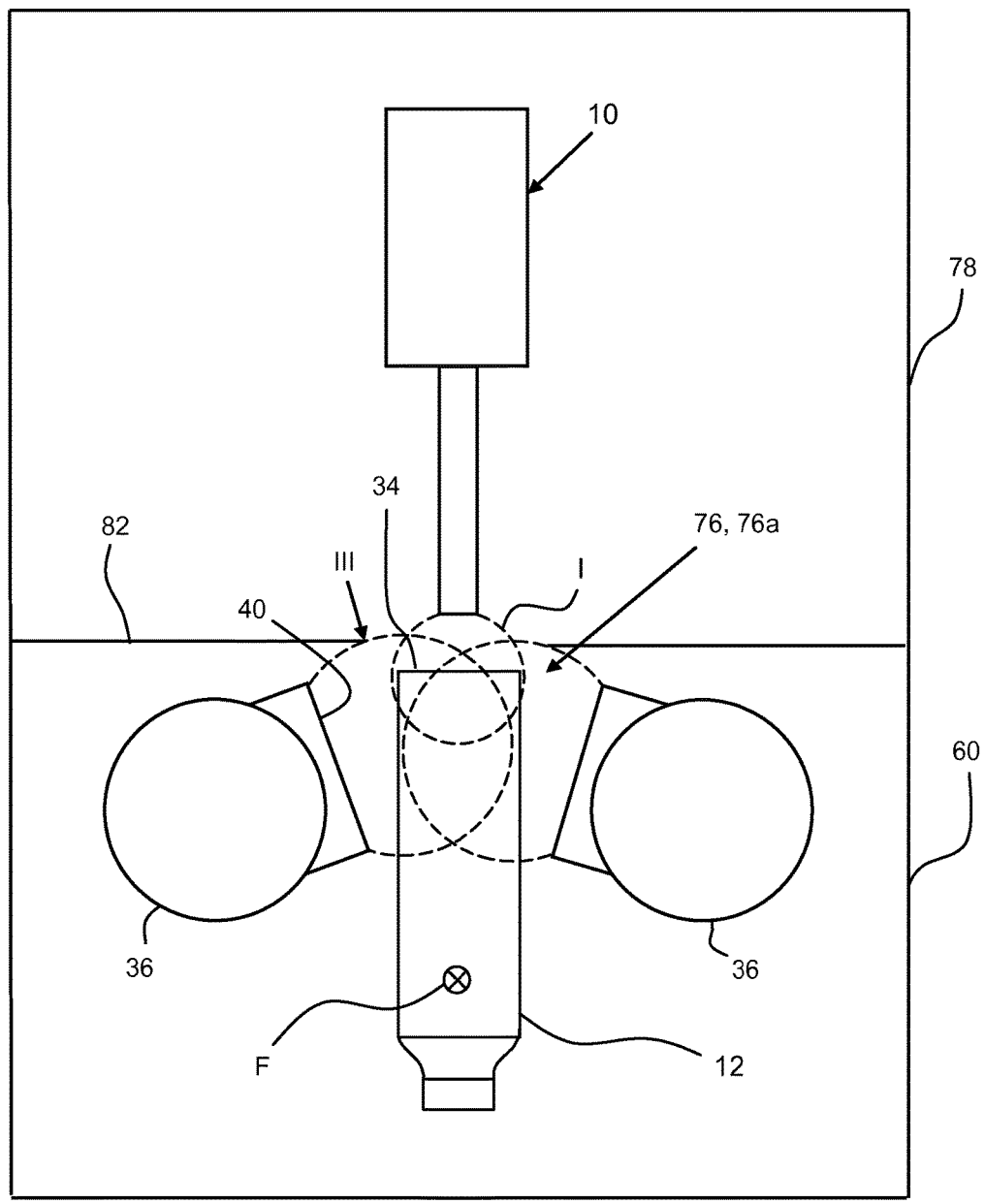
FIG. 3d is a side view of a first end of an entry region according to the exemplary embodiment.

When a packaging container 12 reaches the out-feed position 74 it is directed tangentially and arrives at the first end 76a of the entry region 76. At this point in time the interior sterilization is about to be finalized. During the initial entry of the packaging container 12 into the entry region 76, at the first end 76 thereof, the first electron beam emitter 10 is positioned right above the opening 34 of the packaging container 12. In this moment the electron cloud I emitted from the first electron beam emitter 10 is adapted to temporarily meet and partly overlap the total electron cloud III emitted from the second electron beam emitters 36. The electron clouds I, III of the first and second electron beam emitters form a combined electron cloud and the opening of the packaging container 12 is in this at least temporarily positioned within the combined cloud. This is shown in FIG. 3d.

By letting the electron cloud I of the first electron beam emitter 10 at least partly overlap the electron cloud III of the second electron beam emitters, upon finalising the interior sterilization of the packaging container 12, it can then be ensured that every portion of the packaging container 12 reaching the inside of the aseptic chamber 78 has been fully sterilized. In other words, by creating electron clouds I, III being partly overlapping it is ensured that any microbiological material on the inside surface of the packaging container cannot escape to the outside surface, or vice versa, without being killed.

It should be pointed out that also the electron cloud I of the first electron beam emitter forms an irradiation barrier in itself; an irradiation lock inside the packaging container 12 during sterilization. Since non-sterile packaging containers are fed into the sterilization chamber 60, and since the exterior of the packaging containers do not become sterile until being passed into the aseptic chamber 78, the sterilization cannot be regarded as sterile as such. Hence it is an advantage to have the electron cloud I being able to form an irradiation lock inside the packaging container 12 to protect the already sterilized portion of the packaging container interior from re-infection. No dirt or microbiological material or particle can manage to travel through the cloud I and into the sterilized interior of the packaging container 12 without being killed/sterilized. The volume of the electron cloud I of the first emitter 10 covers the opening 34 of the packaging container 12. Hence, the sterility of the interior, below the electron cloud I, can be assured even during the time when the packaging container 12 is still in the sterilization chamber 60.

In FIG. 3b an aseptic barrier line, denoted P, is shown. The aseptic barrier line P is a virtual boundary between the sterilization chamber 60 and the aseptic chamber 78. At the entry region the line is defined by the end of the electron cloud III of the second electron beam emitters nearest the aseptic chamber 78. When the packaging containers pass that line in the entry region they pass out of the electron cloud III. As can be seen in the figure the line P is inclined at the entry region, just as the second electron beam emitters 36, and is located a distance above the electron exit windows 40. To the right of the entry region the line P is straight and defines a virtual boundary between the sterilization chamber 60 and the aseptic chamber 78. This will be further described later on.

FIG. 3d shows the overlapping electron clouds, the first and second emitters 10, 36 and a packaging container 12 at the first end 76a of the entry region 76. The packaging container 12 is at the first position, meaning that the packaging container and the first electron beam emitter 10 is no longer engaged with each other. Still, the uppermost end of the packaging container 12, being the open bottom end of the packaging container 12, is still affected by the electron cloud I from the first electron beam emitter 10, although the first electron beam emitter 10 is no longer inside the packaging container 12. At the same time the packaging container 12 has been partly passed into the combined electron cloud III of the second beam emitters 36, and a portion of the exterior of the packaging container 12 has already been sterilized by the electron cloud III of the second beam emitters 36.

Figure 3E:
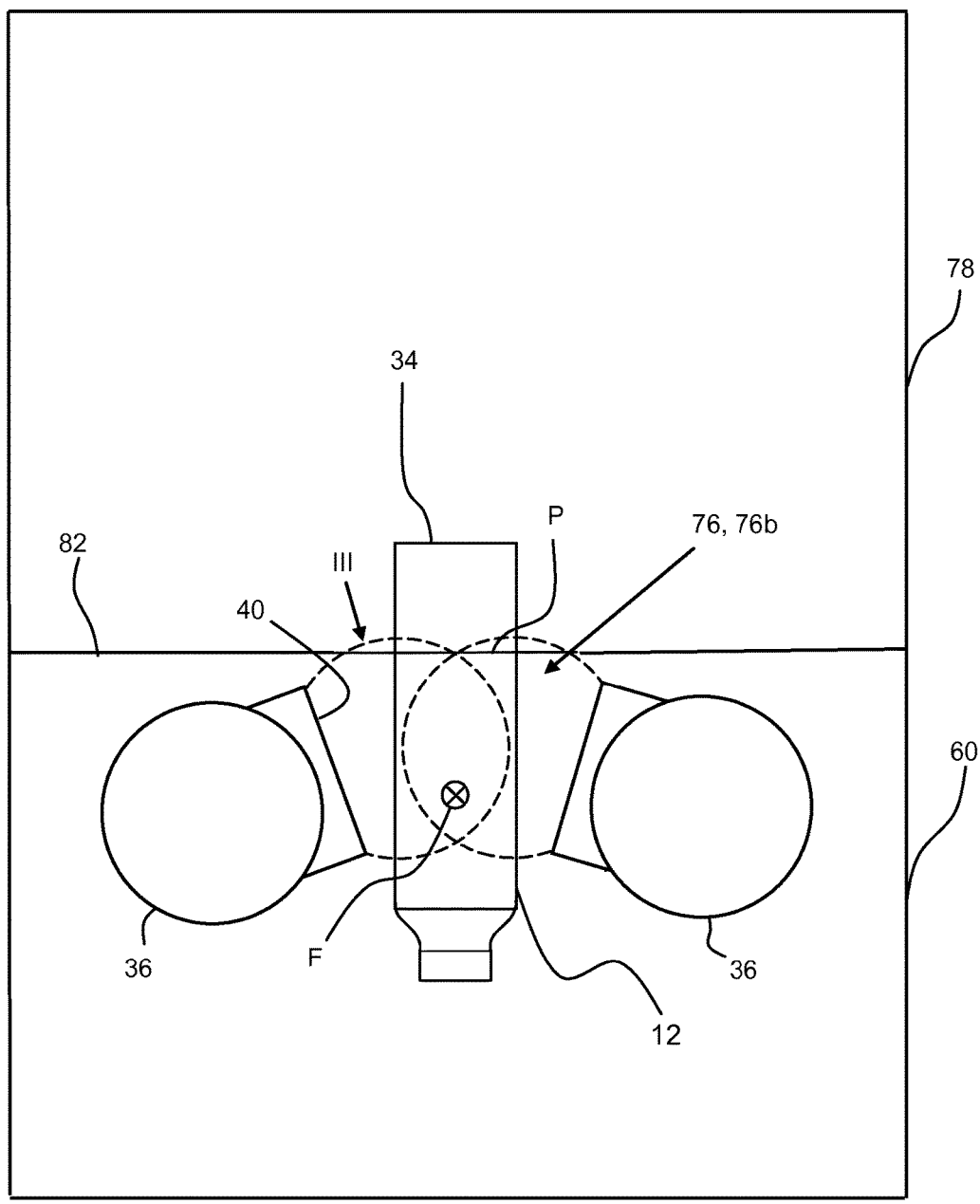
FIG. 3e is a side view, corresponding to FIG. 3d, but of a second end of the entry region.

While the packaging container 12 is fed further into and along the entry region 76, a sterilized portion of the packaging container 12 will gradually leave the entry region 76 and enter the aseptic chamber 78 along the aseptic barrier line P (also seen in FIG. 3b). At a second end 76b of the entry region 76, shown in FIG. 3e, a fully sterilised portion of the packaging container is positioned in the aseptic chamber 78, while a still unsterilized portion is kept outside of the aseptic chamber 78. The length of the sterilized portion protruding in the aseptic chamber 78 is preferably in the interval of about 30-120 mm, as measured from the opening 34 and down along the centre axis of the packaging container 12. Preferably, the length of the protruding portion is 75 mm.

As is shown in the figures the packaging container 12 is fed in the horizontal direction F both in the entry region 76 and in the aseptic chamber 78.

Figure 3F:
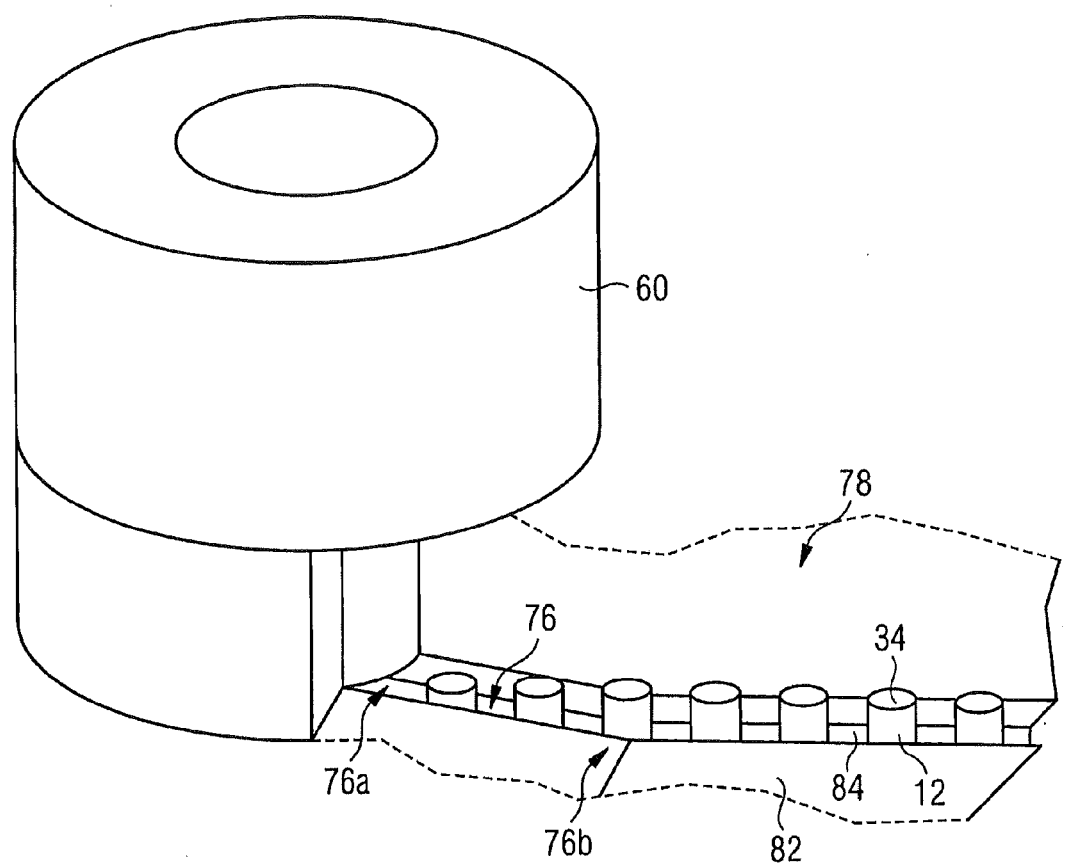
FIG. 3f is a perspective view partly showing a second chamber of the exemplary embodiment.

In FIG. 3f the sterilization device is shown with some of the walls separating the sterilization chamber 60 from the aseptic chamber 78 being visible. As can be seen the aseptic chamber 78 has a bottom wall 82 in which a slot 84 is provided. One portion of the slot 84 is positioned above the entry region 76, and at this portion the surrounding bottom wall 82 is inclined similar to the entry region 76. This inclined bottom wall 82 portion is formed by baffle plates for example made of stainless steel.

In the second chamber 78 the packaging containers 12 are transported along the slot 84 having the sterilized packaging container portion positioned above said bottom wall 82, and the rest of the packaging container positioned below said bottom wall 82.

To secure the aseptic condition in the aseptic chamber 78 a sterile gas flow is provided top-down, i.e. from the second chamber 78 and in a direction downwards through the slot 84. Before the packaging container 12 is fed to the filling station for filling content into the packaging container 12 may be transported past a venting station for ventilating ozone out of the interior of the packaging container. It is a known fact that ozone is created in air during electron beam sterilization, and that it is preferred to remove such ozone before filling product into the packaging containers.

In the following the sterilisation as such is discussed further.

In order for a packaging container to for example reach a sterilization level referred to as "commercially sterile" an absorbed dose of approximately 25 kGy is needed in every point of the interior surface of the packaging container. In the embodiment the interior sterilization is performed during a relative movement between the packaging container and the first electron beam emitter. Hence, the dose has to be calculated by the dose rate (dose delivery per time unit, mentioned as kGy/s) delivered by the emitter and the time each portion of the interior surface of the packaging container is exposed to the electron cloud. An increase in speed of the relative movement will lead to a decrease of the time available for the interior sterilization, and in order to maintain the same dose the dose rate of the emitter needs to be increased. Similar, if the speed of the relative movement is decreased, the time available for sterilization will increase and the dose rate of the emitter will have to be decreased in order not to overexpose the interior surface. In this context any air flows or turbulences in the sterilization chamber need to be taken into account. Air flowing faster than the speed of the relative movement will affect the sterilization result. Such airflow may make a microorganism travel too fast past the electron cloud, which may lead to that microorganism is not being killed. Hence, it is important to control the velocity of the airflows in the sterilization chamber such that it is not higher than the speed of the relative movement. An important aspect is also the flow created in the packaging container because of the relative movement. When the packaging container is lowered from the first electron beam emitter air will automatically be sucked into the packaging container, creating backflow, i.e. an airflow into the packaging container which in some cases may be disturbing for the sterilization effect. To obtain an efficient sterilization and a secure process it has been found that a preferred movement profile comprises a first stage of quickly raising the packaging container to surround the first electron beam emitter, and then a second stage of slowly lowering the packaging container. In other words, the packaging container is moved with a first velocity from the first position to the second position, and with a second velocity from the second position back to the first position, said second velocity being lower than the first velocity. Although the first electron beam emitter is continuously in operation, i.e. continuously emitting electrons, the interior sterilization is considered to be made during the slow lowering of the packaging container. The slow lowering should be slow enough to not create air flows into the packaging container having a velocity higher than that of the relative movement. The volume of the gap between the packaging container and the first electron beam emitter as well as the volume of the first electron beam emitter are factors that influence the velocity of the flows created into the packaging container.

In the embodiment described the first stage of quickly raising the packaging container to surround the first electron beam emitter will take approximately half the time compared to the time spent for the second stage of slowly lowering the packaging container. Hence, the first velocity is approximately twice as high as the second velocity. An exemplary movement profile for the described embodiment starts with a quick raise of the packaging container during 0.4 s. The raise is followed by a pause in 0.1 s during which there is no motion. The movement profile is completed by a subsequent slow lowering of the packaging container during 1 s. Hence a total time of 1.5 s is used for the interior sterilization. Approximately ⅔ of the time is used for the lowering of the packaging container.

The first conveyor 64 is preferably endless and a portion of it is positioned underneath the bottom wall 82 of the aseptic chamber 78 such that the packaging containers 12 can be transported to the filling and sealing stations with one and the same conveyor 64 as used in the sterilization chamber 60. Thereby unnecessary packaging container handovers between conveyors can be avoided.

Although the present invention has been described with respect to several embodiments, it is to be understood that various modifications and changes may be made without departing from the object and scope of the invention as defined in the appended claims.

In the embodiment two second electron beam emitters 36 are shown opposite each other. In an alternative embodiment there is only one second electron beam emitter, and the packaging container is made to rotate approximately one round around its own longitudinal axis when passing through the entry region. In order to ensure an irradiation lock, the opening between the sterilization chamber and the aseptic chamber should not be larger than that the electron cloud, generated by the single second electron beam emitter, can cover the opening.

The sterilization device has been described and illustrated in a schematic way in the above described embodiments and in the drawings. Only parts of the sterilization device being involved in the invention have been described, but it is to be understood that the sterilization device comprises also additional parts such as drive units for driving for example the carrier wheel, the guide wheel and the in-feed wheel as well as the first conveyor. It is also to be understood that the sterilization device comprises an irradiation shield enclosing the sterilization device for securing that electrons and x-rays are not spread to the environment outside of the device.

In the embodiment the packaging containers are carton bottles being sterilized and filled through an open bottom end, and hence that end is the portion of the packaging container being fed into the aseptic chamber. However, it is easily realized that the invention can be applied also for other types of bottles, for example PET-bottles, for which sterilization and filling is made through the spout/neck. As previously mentioned FIG. 1c shows sterilization with an electron beam emitter inserted through the spout/neck of a bottle. In this case the portion of the packaging container being fed into the aseptic chamber is naturally the spout and optionally at least a portion of the bottle top portion (shoulder portion). The interior and exterior sterilization can be made similar to what have been described above. The first electron beam emitter needs to have a first body 18a having a diameter small enough to be inserted into the neck opening of the bottle. Further, the portion of the exterior to be sterilised and entered into the aseptic chamber can be kept relatively small. If the bottle is provided with a neck flange, such as a "neck ring", the division between sterilised and unsterilized can for example be set to the level of the neck ring, i.e. the threaded portion above the neck ring can be sterilized and entered into the aseptic chamber, whereas the portion below the neck ring can be kept unsterilized and below the bottom wall. Similarly, the present invention is of course also applicable to sterilization of plastic bottle preforms, e.g. PET pre-forms. Sterilization of pre-forms is made before they are blow-moulded into a finished PET bottle.

In the described embodiment the first chamber has been described as a sterilization chamber and the second chamber as an aseptic chamber, both aimed for aseptic packaging. In another embodiment, in which the packages are disinfected or hygienically treated, not aiming for aseptic level, i.e. not aiming for commercial sterility, the first chamber can be less clean than the second chamber, and the second chamber not being clean to an aseptic level. In such an embodiment the dose applied by the electron beam emitters is normally lower than the dose used for aseptic packaging, and the word "sterilize" should in that context be interpreted as "hygienically treat" or "disinfect".

The invention claimed is:

1. Sterilization device for sterilizing open packaging containers with electron beams, said sterilization device comprising
   a first chamber comprising at least one first electron beam emitter adapted for sterilization of at least the interior of the packaging container through an opening of the packaging container,
   at least one second electron beam emitter adapted for sterilization of at least a portion of the exterior surface of said packaging container, wherein
   said first chamber having an entry region towards a second chamber, through which entry region a packaging container portion, comprising said opening, is adapted to be passed for entrance into the second chamber,
   said at least one second electron beam emitter being arranged such that its electron exit window is at least substantially facing said entry region, said second electron beam emitter thereby being adapted to sterilize at least any exterior surface of the packaging container portion being passed through the entry region,
   said at least one first electron beam emitter being arranged to sterilize the interior surface before or at the same time as said packaging container portion is entered into the second chamber, and
   an electron cloud emitted by the at least one second electron beam emitter is elongate and defines the entry region, and wherein the entry region is inclined in relation to a feeding direction of the packaging containers and in relation to a longitudinal direction of the packaging containers, such that a greater exterior surface area of the packaging containers passing through the entry region is sterilized.

2. Sterilization device according to claim 1, wherein the first electron beam emitter and the packaging container are adapted to perform a mutual relative movement, during which movement a portion of the first electron beam emitter is temporarily inserted through the opening of the packaging container, such that interior sterilization of the packaging container takes place.

3. Sterilization device according to claim 1, wherein the at least one second electron beam emitter is positioned such that the electron cloud emitted from the at least one second electron beam emitter, during operation of the sterilization device, is adapted to form an irradiation barrier at least covering the entry region, and wherein an electron cloud emitted from the first electron beam emitter is adapted to temporarily meet and partly overlap the electron cloud emitted from the at least one second electron beam emitter, said electron clouds together forming a combined electron cloud, and wherein the opening of the packaging container portion is at least temporarily positioned within the combined cloud.

4. Sterilization device according to claim 1, wherein the at least one second electron beam emitter is arranged such that a longitudinal axis thereof and of the electron exit window is inclined in relation to a horizontal direction, and that the packaging container is moved along said horizontal direction, with a longitudinal centre axis of the packaging container directed perpendicular to the horizontal direction, in such a way that a portion of the packaging container, comprising the opening, is gradually leaving the entry region and entering the second chamber.

5. Sterilization device according to claim 1, wherein the second chamber has a bottom wall provided with a slot, and wherein the packaging containers are transported in the second chamber along the slot having the sterilized packaging container portion positioned above said bottom wall, and the rest of the packaging container positioned below said bottom wall, and wherein a sterile gas flow is provided, during operation, from the second chamber and in a direction towards the slot.

6. Sterilization device according to claim 1, wherein the at least one second electron beam emitter comprises two second electron beam emitters, arranged opposite each other with their electron exit windows facing each other and the entry region, in such a way that the packaging containers can pass in between them.

7. Sterilization device according to claim 1, further comprising a packaging container conveying system comprising a packaging container conveyor comprising holders adapted to hold the packaging containers, and wherein said packaging container conveyor is used for transporting packaging containers both in the first chamber, the entry region and the second chamber.

8. Sterilization device according to claim 7, wherein the packaging container conveying system comprises a rotatable guide wheel adapted to cooperate with a carrier wheel carrying a plurality of said first electron beam emitters and the packaging container conveyor such that each packaging container is adapted to be aligned with a corresponding one of said plurality of said first electron beam emitters, and which guide wheel is provided with packaging container grippers adapted to displace each packaging container in relation to the first electron beam emitter with which the packaging container is aligned between a first position in which the packaging container and the first electron beam emitter with which the packaging container is aligned are not engaged with each other and a second position in which the first electron beam emitter with which the packaging container is aligned is fully inserted into the packaging container.

9. Sterilization device according to claim 8, wherein the packaging container grippers are adapted to lift each packaging container from a corresponding one of said holders to the second position, in which the packaging container is released from said corresponding one of said holders, and then to retract the packaging container to the first position and back into said corresponding one of said holders.

10. Sterilization device according to claim 2, wherein the mutual relative movement is such that the packaging container is moved with a first velocity from a first position to a second position, and with a second velocity from the second position back to the first position, said second velocity being lower than the first velocity.

11. Method of sterilizing open packaging containers with electron beams, said method comprising
   sterilizing at least the interior of the packaging container, through an opening of the packaging container, with a first electron beam emitter arranged in a first chamber,
   sterilizing at least a portion of the exterior of the packaging container with at least one second electron beam emitter, wherein said at least one second electron beam emitter being arranged such that its electron exit window is at least substantially facing an entry region, said entry region forming an entrance to a second chamber from the first chamber, and the sterilizing of at least a portion of the exterior of the packaging container is performed in said entry region by passing a portion of the packaging container, said portion comprising said opening, through the entry region, and the sterilizing of the interior of the packaging container is performed before or at the same time as said packaging container portion is entered into the second chamber, and an electron cloud emitted from the at least one second electron beam emitter is elongate and defines the entry region, and wherein the entry region is inclined in relation to a feeding direction of the packaging containers and in relation to a longitudinal direction of the packaging containers, such that a greater exterior surface area of the packaging containers passing through the entry region is sterilized.

12. Method according to claim 11, further comprising performing mutual relative movement between the first electron beam emitter and the packaging container during which movement the sterilizing of the interior of the packaging container takes place, and during which movement a portion of the first electron beam emitter is temporary inserted through the opening of the packaging container, and wherein the method comprises forming an irradiation barrier at least covering the entry region during operation of the sterilizing device, said irradiation barrier being formed by the electron cloud emitted from the at least one second electron beam emitter, and forming a combined electron cloud by temporarily letting an electron cloud emitted from the first electron beam emitter meet and partly overlap the electron cloud emitted from the at least one second electron beam emitter, and temporarily positioning the opening of the packaging container within the combined electron cloud.

13. Method according to claim 11, wherein the sterilizing of at least the interior of the packaging container and the sterilizing of at least a portion of the exterior of the packaging container are performed in a filling machine, and further comprising filling content into the sterilized packaging container, and sealing the opening after filling.

* * * * *